US00PP33545P2

(12) United States Plant Patent
Volz

(10) Patent No.: US PP33,545 P2
(45) Date of Patent: Oct. 12, 2021

(54) APPLE TREE NAMED 'PREMA003'

(50) Latin Name: *Malus domestica*
Varietal Denomination: PremA003

(71) Applicant: Prevar Limited, Hastings (NZ)

(72) Inventor: Richard Volz, Auckland (NZ)

(73) Assignee: Prevar Limited, Hastings (NZ)

( * ) Notice: Subject to any disclaimer, the term of this patent is extended or adjusted under 35 U.S.C. 154(b) by 0 days.

(21) Appl. No.: 16/974,185

(22) Filed: Nov. 4, 2020

(51) Int. Cl.
*A01H 5/08* (2018.01)
*A01H 6/74* (2018.01)

(52) U.S. Cl.
USPC ..... Plt./161

(58) Field of Classification Search
USPC ..... Plt./161
See application file for complete search history.

*Primary Examiner* — Susan McCormick Ewoldt
(74) *Attorney, Agent, or Firm* — Michelle Bos Legal LLC

(57) ABSTRACT

A new and distinct apple tree named 'PremA003', the fruit of which is notable for its intense red skin color, large size and tender-crisp flesh texture.

1 Drawing Sheet

Latin name: *Malus domestica.*
Variety denomination: PremA003.

BACKGROUND OF THE VARIETY

The new apple tree variety 'PremA003' was created in the course of a planned breeding program carried out at Havelock North, New Zealand. 'PremA003' originated as a result of a controlled cross of seed parent 'Honeycrisp' (U.S. Plant Pat. No. 7,197, expired) and pollen parent 'Sciros' (U.S. Plant Pat. No. 7,814, expired). 'PremA003' was selected as a single plant from among a population of seedlings derived from the parents, and was initially selected for its fruit, which exhibits an intense red skin color, large size and tender-crisp flesh texture. Asexual propagation by budding was first performed at Havelock North, New Zealand. The variety has been observed over a number of asexually propagated generations, and has been found to remain true to type.

'PremA003' is distinguished from parent varieties 'Honeycrisp' and 'Sciros' as set forth in Table 1 below.

TABLE

Comparison of 'PremA003' to Parents

| | 'PremA003' | 'Honeycrisp' | 'Sciros' |
|---|---|---|---|
| Maturity date | Mid-season | Early season | Mid- to late-season |
| Overcolor | Strong red flush over 80%+ of surface | Blotched scarlet over 50% of surface | Solid red flush over 50% of surface |

'PremA003' matures with 'Braeburn' (not patented) and has a light and tender flesh texture similar to 'Honeycrisp'. 'PremA003' is distinguished from similar variety 'Fuji Supreme' ('CABp Fuji', U.S. Plant Pat. No. 17,914) by its lower vigor and fewer blooms.

BRIEF DESCRIPTION OF THE PHOTOGRAPHS

FIG. 1 shows the fruit, branches and leaves of the variety.

DETAILED BOTANICAL DESCRIPTION OF THE VARIETY

The following-detailed botanical description is based on observations made during the 2020 growing season near Yakima, Wash. of 6-year-old trees grown on 'NIC 29' rootstock. All colors are described according to The Royal Horticultural Society Colour Chart (6th ed. 2015). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

*Tree*.—Type Ramified. Habit Spreading. Vigor Moderate. Height 1.5 m. Trunk diameter (at 30 cm above the graft) 2.5 cm. Bark coloration Moderate brown 165A. Bark texture Rough. Lenticel color Moderate orange yellow 165C.

*Branch* (*fruiting branches located at around* 1 *m above the graft union*).—Length 50 cm. Diameter 6 mm. Crotch angle 90°. Bark color Moderate brown 165A. Branch lenticel diameter 0.5 mm. Branch lenticel color Pale yellow 165D. Branch lenticel density About 14 per 10 $cm^2$.

*One year old shoot*.—Length 17.5 cm. Diameter 6 mm. Color Pale yellow 165D. Pubescence Pubescent. Internode length 3.2 cm. Shoot lenticel diameter 1 mm. Shoot lenticel color Pale yellow 165D. Shoot lenticel density 14 per 10 $cm^2$.

*Flower buds*.—Shape Ovate, pointed. Length 14 mm. Diameter 8 mm. Number per cluster 5.

*Flowers*.—Date of first bloom Apr. 5, 2020 (near Yakima, Wash.). Date of full bloom Apr. 13, 2020 (near Yakima, Wash.). Diameter of open flower 35 mm. Depth of open flower 5 mm. Relative position of petal margin Overlapping. Quantity of petals per flower 5. Petal shape Obovate. Petal apex Rounded. Petal base Acute. Petal length 20 mm. Petal width 12 mm. Margin Entire; ruffled. Color of upper surface Yellowish white N155D. Color of lower surface Yellowish white 155B. Pistil length 8 mm. Pistil color Brilliant greenish yellow 2D. Stigma diameter 0.5 mm. Stigma color Pale greenish yellow 1D. Style length 7 mm. Style color Pale greenish yellow 1D. Ovary length 4 mm. Ovary color Moderate yellow green 146B. Stamen quantity About 12. Anther length 1 mm. Pollen Present, dark reddish orange 175B. Pedicel length 8 mm. Pedicel diameter 3 mm. Pollinator Required.

*Sepals*.—Quantity 5. Color Light yellow green 145C. Length 6 mm. Shape Triangular, pointed.

*Leaves*.—Shape Ovate. Apex Acuminate. Base shape Aequilateral. Length 13 cm. Width 8 cm. Blade margin Serrate. Color of upper surface Moderate yellowish green 139B. Color of lower surface Greyish yellow green 191B. Texture of upper surface Smooth. Texture of lower surface Smooth with raised veins. Arrangement Alternate.

*Petiole*.—Length 2 cm. Diameter 1 mm. Color Moderate purplish red 59C. Stipule length 12 mm. Stipule width 1 mm. Stipule color Strong yellow green 145A.

*Fruit*.—Quantity per cluster 5. Diameter 78 mm. Height 77 mm. Weight Large, 280 g. General shape in profile Broad conic, tending toward globose. Position of maximum diameter Above equator. Ribbing None. Crowning at calyx end None. Aperture of eye Somewhat open. Depth of eye basin 9 mm. Width of eye basin 25 mm. Length of sepal 4 mm. Bloom of skin Present. Greasiness of skin Not greasy. Background color of skin Brilliant yellow green 150C. Amount of over color 80%+. Over color of skin Strong red 53D. Intensity of over color Moderate, intensifies with maturity. Pattern of over color Solid flush. Skin texture Smooth. Lenticels Abundant, prominent, diameter 1 mm. Amount of russet around stalk cavity None. Amount of russet on cheeks None. Area of russet around eye basin None. Length of stalk 16 mm. Diameter of stalk 2 mm. Depth of stalk cavity 10 mm. Width of stalk cavity 18 mm. Stalk color Strong yellow green 144B. Flesh texture Fine, crisp. Aroma Slightly sweet. Juiciness Juicy. Flesh color Pale greenish yellow 2D. Core length 30 mm. Locule length 15 mm. Locule diameter 10 mm. Locule shape Oval with pointed tip.

*Seeds*.—Quantity per fruit About 11. Shape Teardrop. Length 13 mm. Width 5 mm. Color Greyish brown 166A. Pest and disease resistance None noted. Pest and disease susceptibility None noted. Winter hardiness Hardy in area tested.

*Harvest*.—Time for harvest Mid-season, Sep. 14 to 24, 2020. Yield 25 to 58 metric tons per hectare (about 10 to 23 tons per acre). Storage Long storage life, about 20 weeks; some internal browning (5%).

*Market use*.—Fresh eating.

I claim:

1. A new and distinct apple tree substantially as described and illustrated herein.

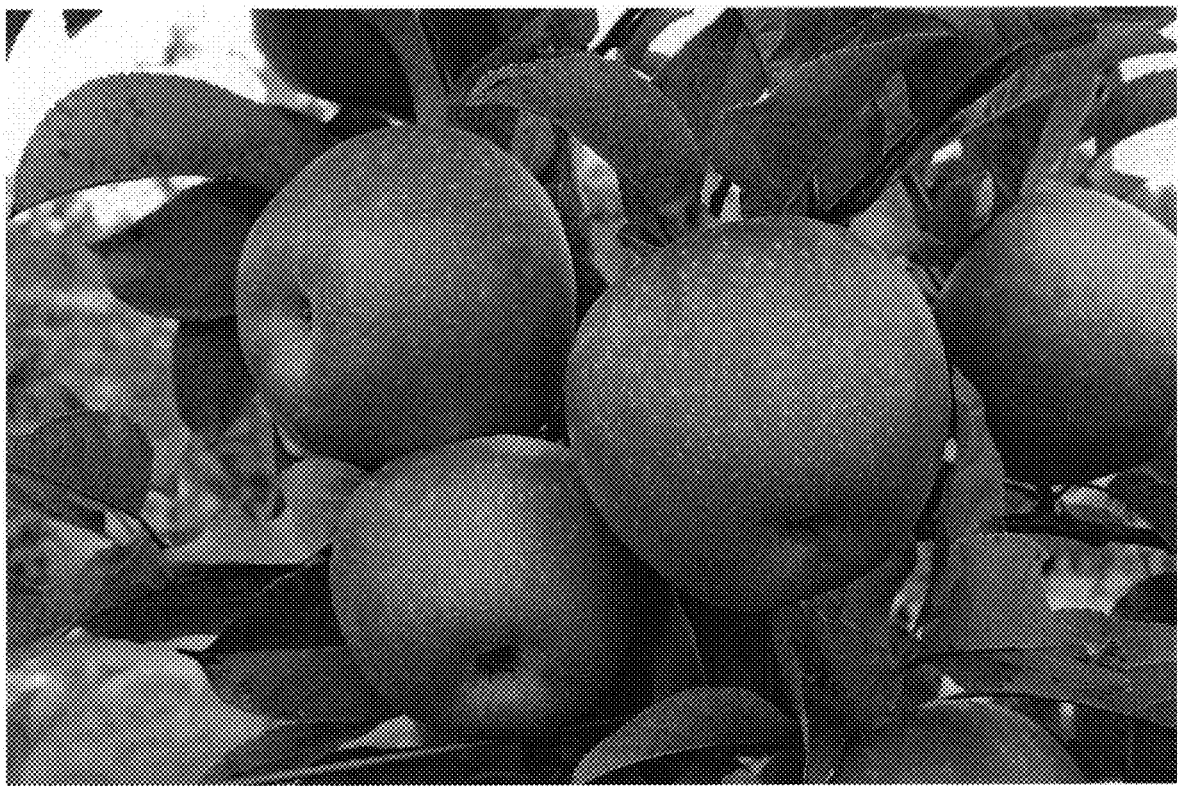

* * * * *